United States Patent [19]

Isacoff et al.

[11] Patent Number: 5,756,351

[45] Date of Patent: May 26, 1998

[54] BIOMOLECULAR OPTICAL SENSORS

[75] Inventors: Ehud Y. Isacoff; Lidia M. Mannuzzu; Mario M. Moronne, all of Berkeley, Calif.

[73] Assignee: The Regents of the University of California, Oakland, Calif.

[21] Appl. No.: 783,377

[22] Filed: Jan. 13, 1997

[51] Int. Cl.$^6$ .............................. C12N 5/00; C12N 1/20; C12N 3/00; C12N 1/14

[52] U.S. Cl. ................. 435/325; 435/242; 435/252.3; 435/254.11; 435/257.2; 435/410

[58] Field of Search ........................ 435/325, 252.3, 435/242, 254.11, 257.2, 410

[56] References Cited

PUBLICATIONS

Mannuzzu et al. (1996) Science 271, 213–216. Direct physical measure of conformational rearrangement underlying potassium channel gating.

Gether et al. (1995) J Biol Chem 270, 28628–28275. Fluorescent labeling of purified $\beta_2$Adrenergic receptor.

Turcatti et al. (1996) J Biol Chem 271, 19991–19998. Probing the Structure and Function of the Tachykinin Neurokinin–Receptor through Biosynthetic incorporation of flourescent amino acids at specific sites.

Liu et al. (1996) Biochemistry 35, 11865–11873. Site–Directed fluorescent labeling of P–glycoprotein on cysteine residues in the nucleotide binding domains.

Baba et al. (1986) Chemical modification and fluorescence labeling study of Ca2 + –adenosine triphosphatase of sarcoplasmic reticulum using iodoacetamide and its N–substituted derivatives. Journal of Biochemistry 100(5): 1137–1147. Jun. 1986.

Kaback et al. (1994) The lactose permease meets Frankenstein. Journal of Experimental Biology 196: 183–195. Jan. 1994.

Kaback et al. (1993) What's new with lactose permease. Journal of Bioenergetics and Biomembranes 23(6): 627–636. Jan. 1993.

Ngo et al. (1994) Computational Complexity. Protein Structure Prediction, and the Levinthal Paradox. In: The Protein Folding Problem and Tertiary Structure Prediction. Eds. Merz et al., Birkhauser, Boston, MA, pp. 491–495. Jan. 1994.

Rudinger (1976) Cahracteristics of the amino acids as components of a peptide hormone sequence. In: Peptide Hormones. Ed. J. A. Parsons. University Park Press, Baltimore, MD. pp. 1–7. Jun. 1976.

Glazer et al. (1986) Site–specific modification of native proteins with group–specific reagents. In: Chemical Modification of Proteins: Selected methods and analytical procedures. Elsevier Biomedical Press. New York, NY. pp. 121–122, Apr. 1986.

Alexiev et al. (1994) Covalently bound pH–indicator dyes at selected extracellular or cytoplasmic sites in bacteriorhodospin. 2. Rotational orientation of helices D and E and kinetic correlation between M formation and proton release in bacteriorhodops. Nov. 22, 1994.

*Primary Examiner*—Robert A. Wax
*Assistant Examiner*—Einar Stole
*Attorney, Agent, or Firm*—Richard Aron Osman

[57] ABSTRACT

The invention provides protein-based sensors which report changes at a cell surface membrane. These sensors comprise an endogenous cell surface protein having a post-translationally generated luminescer at a predetermined residue. In operation, the protein adopts one of a plurality of different interconvertable signal-dependent conformations, whereunder the luminescer provides corresponding different luminescence. The cells comprise transgenes encoding the protein sensor which is translated from such transgenes by the host cell's machinery with natural amino acids and expressed on the cell surface. After surface expression, the cell is contacted with a luminescer generating reagent which generates a luminescer at a predetermined residue of the protein. A wide variety of luminescers and chemistries for generating the selected luminescer at the target residue of the sensor protein may be used.

8 Claims, No Drawings

BIOMOLECULAR OPTICAL SENSORS

FIELD OF THE INVENTION

The field of the invention is protein-based luminescent labels.

BACKGROUND

Existing methods for monitoring the physiological status of a cell include microscopy, specific labeled binding probes such as antibodies, ion-specific or voltage-sensitive dyes, electrical instruments such a patch clamps, etc. Some of these techniques require fixation, disruption or isolation of the cells of interest; others can not provide real-time analysis; and others require sophisticated instrumentation or specific reagents. Needed are broadly applicable methods for evaluating the status of cell physiology in real time.

RELEVANT LITERATURE

Mannuzzu et al. (1996) Science 271, 213–216 describe the direct physical measure of conformational rearrangement underlying potassium channel gating using an optically-tagged channel protein. Gether et al. (1995) describe the fluorescent labeling of soluble purified $_2$ Adrenergic receptor to detect ligand-specific conformational changes. Turcatti et al. (1996) describe the incorporation of non-natural flourescent amino acids into a receptor to monitor ligand binding. Liu et al. (1996) describe fluorescent labeling of soluble purified P-glycoprotein to detect ligand binding.

SUMMARY OF THE INVENTION

The invention provides methods and compositions for monitoring the physiological status of a cell. In particular, the invention provides protein-based sensors which report changes at a cell surface membrane. Reportable changes, or signals, include ligand binding, changes in charge distribution across the plasma membrane (e.g. membrane depolarization), changes in protein-protein interactions (particularly interactions involving the sensor), post-translational modifications of the sensor, membrane deformation, etc.

The subject compositions include cells comprising artificial molecular optical sensors. These sensors comprise an endogenous cell surface protein having a post-translationally generated luminescer at a predetermined residue. In operation, the protein adopts one of a plurality of different interconvertable signal-dependent conformations, whereunder the luminescer provides corresponding different luminescence. The cells may be in culture, resident in a tissue or animal, etc. In addition, the invention comprises methods of making and using the subject cells.

The subject cells comprise transient or stable transgenes encoding the protein sensor which is translated from such transgenes by the host cell's machinery with natural amino acids and expressed on the cell surface. After surface expression, the cell is contacted with a luminescer generating reagent which generates a luminescer at a predetermined residue of the protein. A wide variety of luminescers and chemistries for generating the selected luminescer at the target residue of the sensor protein may be used. For example, functionally available sulfydryl groups are conveniently targeted with preluminescers comprising sulfhydryl groups under conditions where the sulfhydryls form disulfide linkages, or by iodoacetamides or maleimides which also conjugate with high chemical specificity. Frequently, the target residue is a mutational insert, i.e. not native to the protein. For example, in the case of disulfide linked luminescers, a non-native cysteine residue may be incorporated into the sensor protein.

Similarly, it is often advantageous to limit luminescer generation to the target site by minimizing the presence of other otherwise functionally available sites, both on the sensor protein and other surface proteins of the cell. For example, in the case of disulfide-linked luminescers, otherwise available native cysteine residues may be eliminated by genetic or chemical ablation. In a particular embodiment, such surface ablation is preceded by subjecting the cell to conditions which temporarily block the expression of nascent proteins on the cell surface.

The subject methods permits the direction of the sensors genetically to select locations during specific developmental times, and provides enhanced percentage fluorescence changes and improved signal to noise ratios. Additionally, by targeting sensors to specific cell types the role of those cells can be selectively assessed, and background signals eliminated (e.g. voltage changes in glial cells during optical recordings of electrical activity in the brain resulting from potassium released by neurons). Since the sensors can be targeted to specific subcellular compartments different phases of a given transduction event can be monitored individually (e.g. synaptic potentials in dendrites versus action potentials in axons; or ion flux into epithelial cells at the basolateral membrane versus efflux at the apical membrane). Moreover, the ability to choose versions of the sensor protein that have distinct ranges over which they respond to a biological signal (e.g. voltage-shifted mutants of voltage-gated channel), or the response time of the sensor (e.g. the rate at which channels open in response to a voltage change) permits the exclusion background events.

DETAILED DESCRIPTION OF THE INVENTION

The subject sensors comprise an endogenous (i.e. produced by the host cell) cell surface protein having a post-translationally generated luminescer at a predetermined residue. A wide variety of cell surface proteins, preferably transmembrane proteins, can be used in the sensors, including membrane channel proteins such as ion channels, receptors such as cytokine receptors, signal transducing proteins such a G-proteins and kinases, etc. The selected protein must be capable of adopting a plurality of different interconvertable signal-dependent conformations and provide a suitable target residue for localizing the luminescer. The target residue is selected to provide different microenvirons for the luminescer corresponding to the different protein conformations, which in turn correspond to different cellular states which correspond to different signals, such that the luminescer provides corresponding different luminescence. It is important that generation of the luminescer does not perturb the function of the protein sought to be monitored. For example, residues comprising pores or ligand binding sites are avoided. For most employed chemistries, the target residue is necessarily located on the extracellular portion of transmembrane proteins. Target residues are readily determined empirically. Frequently, the target residue is a mutational insert, i.e. not native to the protein, at a predetermined site, generally away from ligand binding residues yet accessible to the luminescer generating reagent. Methods for site-directed mutagenesis of membrane proteins are well known in the art.

The subject cells comprise transient or stable transgenes encoding the protein sensor which is translated from such transgenes by the host cell's machinery with natural amino acids and expressed on the cell surface. The cells may be in culture, resident in a tissue or animal, etc. Methods for transiently and stably transfecting cells, including ES cells and zygotes, and the production of transgenic animals are well known in the art.

After surface expression, the cell is contacted with a luminescer generating reagent which generates a luminescer, preferably a fluorescer, at a predetermined residue of the protein. A wide variety of luminescers and chemistries for generating the selected luminescer at the target residue of the sensor protein may be used. Exemplary luminescers include fluorescein, MIANS, eosin, lanthanide-based dyes, bromobimame, etc. Many suitable luminescers are commercially available from Molecular Probes, Inc. The luminescer generating reagent may comprise a luminescent reagent which directly covalently couples to a functional group of the target residue, a preluminescent reagent which acquires the assayable luminescent properties after coupling to or reaction the target residue; reactants and/or enzyme which react with the residue to form a luminescent product or complex, etc. For examples, in addition to the cysteine chemistries described above and exemplified below, N-terminal serine or threonine residues may be targeted via reduced Schiff base formation; the epsilon-amino group of lysine residues by isothiocyanates, sulfonyl chlorides, activated carparanitrophenolic esters, etc.; tyrosine residues via nitration with tetranitromethane; glutamine with transglutaminase, etc.

It is often advantageous to limit luminescer generation to the target site by minimizing the presence of other otherwise functionally available sites, both on the sensor and other surface components, including other surface proteins. Otherwise available residues other than that targeted may be eliminated by genetic or chemical ablation. Generally, chemical ablation involves preblocking with a non-luminescent reagent which reacts with, and blocks, residues that would otherwise be subject to the luminescer generating reagent. Suitable blocking agents for given functional groups are well known in the art; the precise selection of which is determined by the chemistry used by the luminescer generating reagent. Generally, when preblocking is used such surface ablation is preceded by subjecting the cell to conditions, such as reduced temperature incubation, which temporarily block the expression of nascent proteins on the cell surface.

Numerous advantages of the disclosed biosensors and methods are evident. For example, expression of the sensors are conveniently targeted to specific cell types and developmental stages in vivo using specific promoters, thus allowing for measurements of activity to be made from subsets of cells in a tissue, such as specific cells in a neural circuit. Since the signal comes only from the cells of interest which are expressing the sensor gene, background fluorescence from other cells, which often presents a major problem for detection of small signals, is entirely eliminated. These cells are readily isolated and cultured for in vitro assays of chemical or developmental interactions.

In addition, the sensors can be stably incorporated into clonal cell lines by integration of the genes that encode them into the genome thus allowing the cells to be used in transient transfection assays for the functional isolation or pharmacological characterization of new gene products. Also, protein localization signals are fused to the sensors to produce versions targeted to specific membrane locations within cells (e.g. select intracellular organelles or plasma membrane) as well as to select regions within a cell (such as apical versus basolateral membrane in epithelial cells, or dendrites versus axons in neurons) to selectively report on signaling events within that cellular compartment. In addition, since the sensitivity and range of operation of our sensors is biologically determined they are able to detect biologically relevant signals. They are also easily calibrated so that their fluorescent output can be translated into units of activity. Also, mutagenesis is used to make variants of these sensors that operate with distinct response times and ranges of sensitivity, making it possible to dissect apart specific components of a cellular signal in complex signaling events. In addition, the signal to noise of this method is vastly superior to prior art methods. In the embodiment exemplified below, the channel F/F is 15–100%, orders of magnitude better than voltage-sensitive dyes, which have a F/F of about 0.1%. In addition, unlike the chemical dyes, the subject sensors are not toxic to cells. Finally, the sensors can be labeled with a variety of commercially available fluorophores for greater flexibility of assay.

Cells comprising the subject sensors are particulary suitable for high-flux sample screening with applications in toxicology, food and environmental monitoring, drug screening, etc. For example, the subject sensors can be transfected transiently or stably into high expression cell lines (e.g. CHO, COS, HEK 293, NIH 3T3, etc.) and either the native cellular machinery of these cells, or of co-transfected genes, can then be assayed. The screens can be performed at a high rate by automated means which involve exposure to specific chemical signals and monitoring of luminescent emission. e.g. fluorescence. Suitable instrumentation and methods for plate scanning, or multichannel perfusion using conventional indicators are known in the art.

Advantages of high throughput assays of bio-active drugs include: minimal steps required to set up an assay—transfected cell lines can be plated and challenged; reliable repetitions of the assay—for example, tetramethylrhodamine is very resistant to bleaching and has a very large F/F, thus allowing for quantitative repetition of assay; optical method makes it possible to assay multiple samples simultaneously; the sensitivity and kinetics of the assay are readily optimized by mutagenesis, providing unique flexibility; and, the ability to easily switch the assay between different biological preparations allows for assay optimization.

The following examples are offered by way of illustration and not by way of limitation.

EXAMPLES

Direct Physical Measure of Conformational Rearrangement underlying Potassium Channel Gating using Sensors According to the Invention Since voltage-gated ion channels were first cloned, it has been postulated that the positively charged S4 segment functions as the voltage-sensor (1). Membrane depolarization is hypothesized to open the channel by moving S4 outward, thus generating the gating current. In keeping with this model, mutations that alter the charge of amino acids in S4 affect the voltage-sensitivity of channel opening (2, 3). However, these studies could not prove that S4 contains the gating charge because the voltage-sensitivity of channel opening can also be affected by changes in the cooperativity or equilibria of gating transitions (4). In the S4 region of a skeletal muscle $Na^+$ channel, one amino acid position has increased accessibility to the extracellular solution during membrane depolarization (5). This suggests that S4 may move, without explaining how or during which gating transition (activation, opening, or inactivation). The primary prediction of the S4 hypothesis—a correlation between S4 movement and movement of the gating charge—remains to be tested.

To address this problem, we have developed a fluorescence technique to study conformational changes of the Shaker $K^+$ channel S4 during gating in Xenopus oocytes. This technique relies on the sensitivity of many fluorophores to their local environment and on the short lifetime of their excited state (6). Fluorescent labels conjugated to residues in S4 could report changes in environment if activation moves them from a position buried in membrane into the extracellular fluid, as has been proposed (4, 7). To covalently label the channel with a fluorophore (8), cysteine was substituted at positions 346, 356, 359, 365, and 366 of a non-conducting (W434F) (9), non-inactivating (D6-46) (10) version of the Shaker ShH4 $K^{3o}$ channel (11), following the removal of two native cysteines (C245V in S1 and C462A in S6), which could be accessible to the external solution. Cysteines present in endogenous oocyte plasma membrane proteins were blocked with a non-fluorescent and impermeant maleimide (8). Oocytes injected with comparable amounts of cRNA encoding each of the mutant channels were labeled with the membrane-impermeant tetramethylrhodamine-maleimide (TMRM) (8), and membrane fluorescence was quantitated by confocal microscopy. Integration of the fluorescence over the focused membrane area showed between 2.5- and 5.0-fold greater labeling ($p<0.0001$) of the plasma membrane of oocytes expressing the cysteine-added mutants compared to both uninjected oocytes and oocytes expressing the cysteine-removed control channel. The degree of labeling was comparable for S346C, M356C, A359C, and R365C, but it was significantly lower ($p<0.02$) for the position furthest toward the COOH-terminal end of S4 (L366C). Since the channel density of L366C, as judged by measurement of whole-cell gating currents (8), was similar to the other cysteine-added mutants, the lower level of L366C labeling is probably due to a less accessibility of this position to external TMRM. Specific labeling of the cysteine-added mutants was confirmed by fluorescence analysis of membrane proteins from labeled oocytes, immune-precipitated and separated by polyacrylamide gel electrophoresis, which showed a broad rhodamine-labeled band of 110 to 115 kD (corresponding to the completely glycosylated Shaker protein) (12) present only in these mutants.

The model proposed for $K^+$ channel gating suggests that a portion of S4 that is buried in the resting state becomes exposed to the external solution by activation (7). To test this model, oocytes expressing S346C, A359C, and R365C were incubated with TMRM in a hyperpolarizing NMGMES solution ($V_{rest}$=-58.7±11.6 mV; mean±SD; n=12), and a depolarizing $K^+$-MBSH solution ($V_{rest}$=1.2±5.4 mV; mean±SD; n=17) (8). The charge-voltage (Q-V) relations measured for these mutants indicate that S346C and A359C will be primarily in the resting state in NMGMES, but would be activated most of the time in $K^+$-MBSH, while R365C would also be in the resting state in NMGMES, but only be activated about 40% of the time in $K^+$-MBSH. Under these conditions, S346C was equally labeled when depolarized or hyperpolarized, A359C was significantly more labeled ($p<0.005$) when depolarized, and R365C was labeled when depolarized, but not when hyperpolarized. Thus, membrane depolarization increases the exposure of positions 359 and 365 to the extracellular solution, whereas position 346 is equally exposed under depolarizing and hyperpolarizing conditions (13). The partial labeling of A359C in the hyperpolarizing solution may be due to the fact that it is activated about 10% of the time in this solution.

During the prolonged depolarization of the $K^+$-MBSH incubation, channels are expected to spend part of their time in the C-type inactivated state (14). To determine whether it is activation, rather than C-type inactivation, that increases the surface exposure of S4, we examined the effect of short depolarizations (producing no C-type inactivation) on S4 access to the extracellular solution. Surface exposure of S4 was monitored by taking advantage of the sensitivity of fluorophores to the polarity of their environment (6). For TMRM, increasing the polarity of the solvent from ethanol (e=24) to water (e=78) decreased peak fluorescence by 33% and shifted the peak from 567 to 575 nm. This indicated that it should be possible to observe a change in fluorescence if TMRM, conjugated to S4, moved into the polar extracellular fluid from a buried, less polar environment.

To examine the relation between changes in the environment of S4 and gating charge displacement, fluorescence of labeled oocytes and whole-cell gating current were measured in parallel under two-electrode voltage clamp (15). At negative holding potentials, membrane fluorescence was higher for oocytes expressing the cysteine-added mutants compared to cysteine-removed controls and uninjected oocytes. On average, the fluorescence at a negative holding potential of -80 mV was comparable for the S346C, M356C, A359C, and R365C mutants, but lower for the L366C mutant, in agreement with the confocal measurements. A series of depolarizing voltage steps moved gating charge for each of the mutants. For several of the mutants, the steps evoked a graded and saturating decrease in fluorescence, which followed the kinetics of the gating current. The maximal decrease in fluorescence was about 10% for M356C and A359C, and 5% for R365C. There was almost no change for S346C ($<1\%$), and no fluorescence change was observed for L366C, or for uninjected oocytes whose endogenous membrane sulfhydryls were left unblocked before labeling with TMRM. For the mutants with the largest fluorescence change (M356C, A359C, and R365C) the fluorescence-voltage relation (F-V) closely correlated with the charge-voltage relation (Q-V), but not with the voltage-dependence of channel opening measured from these mutants in a conducting background. It is unlikely that the observed fluorescence changes are due to a direct effect of the voltage-clamp steps on the energy levels of TMRM, since field perturbations of the fluorophore would neither be expected to saturate nor to correlate with gating charge movement. Instead, these fluorescence decreases most likely reflect a change in the environment of the fluorophore tethered to 356, 359 or 365, when these sites move during activation. These results indicate that channel activation, rather than inactivation or opening, is responsible for the observed increase in S4 exposure to extracellular TMRM.

If the fluorescence decrease is caused by the movement of TMRM conjugated at sites 356 to 365 from a position buried within the membrane into the extracellular solution, then extracellular quenchers should enhance the fluorescence decrease. To test this, we examined the effect of external iodide, a membrane impermeant collisional quencher (16). Iodide enhanced the fluorescence change of A359C by 3.6-fold ($p<10^{31\ 5}$), but did not significantly affect the fluorescence change of the other mutants, although the small sample size may explain the lack of significance of M356C. Thus, activation clearly exposes TMRM conjugated at A359C to extracellular iodide.

Several biophysical models have been constructed to explain the gating of the Shaker $K^+$ channel (4, 17–19).

These models, based on ionic and gating-current measurements, propose two or more major sets of charge carrying transitions. To investigate further the relation between movement of S4 and movement of the gating charge, we examined the effect on the 359C fluorescence of the S4 mutation L382V, which alters just one of the charge carrying steps in channel activation (3, 4, 18). The double mutant A359C/L382V had an effect similar to that described earlier for L382V alone (3, 4, 18); it accelerated gating current kinetics and decreased the slope of the Q-V. Unlike L382V, however, the Q-V of A359C/L382V was not resolved into two clearly separated components, possibly as a result of the A359C mutation or the TMRM conjugation. As with the gating current, A359C/L382V accelerated the rate of the fluorescence change, and the slope of the F-V was decreased in parallel to that of the Q-V. This observation indicates that the change in the environment of S4 follows all of the movement of the gating charge, even in a mutant that shifts one component of the charge movement.

In summary, we find that (i) L366C is less efficiently conjugated by TMRM than the other sites that we have examined, (ii) conjugation by TMRM of A359C and R365C, but not of S346C, is increased by depolarization, (iii) M356C, A359C, and R365C show a fluorescence change that correlates with gating charge displacement, whereas S346C and L366C show little or no fluorescence change, and (iv) TMRM conjugated at A359C becomes accessible to iodide upon activation. These observations are consistent with the model that S4 contains the gating charge and that activation consists of the movement of the outer ($NH_2$-terminal) portion of S4 into the extracellular fluid from a position that is buried in the resting state, thus generating the gating current. In this process, a stretch of at least ten residues (356 to 365), about half of the nineteen residues commonly predicted to make up S4 (7), experiences a change in environment. For at least seven of these residues (359 to 365) the change in exposure to the extracellular fluid is sufficiently extreme to govern whether the site can be conjugated by TMRM. A residue on the $NH_2$-terminal side of this stretch (346) is always exposed, while one on the COOH-terminal side (366) remains partly buried even when the channel is activated. This large-scale S4 movement agrees in essence with the model proposed by Durell and Guy (7) and is consistent with the large charge movement that occurs during gating (12 to 16 charges per channel) (3, 4, 19, 20).

To date, the only structural information available about the nature of the conformational change associated with ion channel gating has been for the bactericidal protein colicin Ia (21), nicotinic acetylcholine receptor (22), and the $Na^+$ channel (5). These studies were limited to a comparison of the endpoints of the gating conformations. The fluorescence technique described here provides information about the transition through conformational intermediates between these endpoints, by tracking, with submillisecond resolution, the motion of specific domains of the channel protein, as gating proceeds. This technique, in conjunction with labeling at other locations, should aid in the structural characterization of gating domains, and shed light on conformational rearrangements that have so far been "invisible" because they neither move charge, nor directly open or close the channel.

References and Notes

1. M. Noda et al. *Nature* 312, 121 (1984); W. A. Catterall *Ann. Rev. Biochem.* 55, 953 (1986); R. E. Greenblatt, T. Blatt, M. Montale *FEBS Lett.* 193, 125 (1985); H. R. Guy, and P. Seetharamulu *Proc. Nat. Acad. Sci. U.S.A.* 83, 508 (1986).
2. W. Stühmer et al., *Nature* 339, 597 (1989); D. M. Papazian, L. C. Timpe, Y. N. Jan, L. Y. Jan, *Nature* 349, 305 (1991); E. R. Liman, P. Hesse, F. W. Weaver, G. Koren, ibid. 353, 752 (1991); D. E. Logothetis et al., *Neuron* 8, 531 (1992).
3. N. A. Schoppa, K. McCormack, M. A. Tanouye, F. J. Sigworth, *Science* 255, 1712 (1992).
4. F. J. Sigworth, *Quart. Rev. Biophys.* 27,1 (1994).
5. N. Yang and R. Horn, *Neuron* 15, 213 (1995).
6. J. R. Lakowicz, *Principles of Fluorescence Spectroscopy* (Plenum Press, New York, 1983).
7. S. R. Durell and H. R. Guy, *Biophys. J.* 62, 238 (1992).
8. Defolliculated, injected Xenopus oocytes were incubated for 3 to 4 days at 12° C., treated with 1 mM tetraglycine maleimide (TGM) in MBSH (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM Hepes, pH 7.5) for 1 hour at 21° C. to block native membrane sulfhydryls, incubated for 12 to 14 hours at 21° C. to permit channels to reach the plasma membrane, and labeled with 5 μM TMRM (Molecular Probes) in $K^+$-MBSH (100 mM KCl, 1.5 mM $MgCl_2$, 0.5 mM $CaCl_2$, 10 mM Hepes, pH 7.5) for 30 min on ice. Two-electrode voltage clamping was with a Dagan CA-1 amplifier in MBSH or in NMGMES [110 mM NMGMES (N-methyl-D-glucamine methanesolfonic acid), 1 mM $Ca(MES)_2$, 10 mM Hepes, pH 7.1]. Whole-cell gating charge was calculated by subtraction of the linear capacitative component from the integral of the off-gating current. Confocal images were acquired with a Biorad MRC-1000 inverted confocal microscope in photon counting mode with a 20×objective.
9. E. Perozo, R. MacKinnon, F. Bezanilla, E. Stefani, *Neuron* 11,353 (1993).
10. T. Hoshi, W. N. Zagotta, R. W. Aldrich, ibid. 250, 533 (1990).
11. A. Kamb, J. Tseng-Crank, M. A. Tanouye, *Cell* 50, 405 (1987).
12. L. Santacruz-Tolosa, Y. Huang, S. A. John, D. M. Papazian, *Biochemistry* 33, 5607 (1994).
13. L366C had a $V_{1/2}$ of activation of −53.8±1.8 mV (mean±SEM, n=5), indicating that channels would be mainly activated during the TMRM incubation.
14. L. C. Timpe, Y. N. Jan, L. Y. Jan, *Neuron* 1, 659 (1988); E. Y. Isacoff, D. Papazian, L. Timpe, Y. N. Jan, L. Y. Jan, *Cold Spr. Hrb. Symp. Quant. Bio.* 55, 9 (1990); L. E. Iverson, B. Rudy, *J. Neurosci.* 10, 2903 (1990); T. Hoshi, W. N. Zagotta, R. W. Aldrich, *Neuron* 7, 547 (1991).
15. Fluorescence was measured with a Hamamatsu HC120-05 photomultiplier tube connected to a Nikon DIAPHOT-TMD inverted microscope with TMD-EF Epi-Fluorescence Attachment and a Chroma High Q TRITC filter, and it was digitized at 20 kHz and low-pass filtered at 1 kHz with an 8-pole Bessel filter. Each response is an average of 5 to 10 traces.
16. In solution, replacement of 50 mM KCl of $K^+$-MBSH with 50 mM KI decreased peak fluorescence of 5 mM TMRM by 40%.
17. E. Stefani, L. Toro, E. Perozo, F. Bezanilla, *Biophys. J.* 66, 996 (1994); F. Bezanilla, E. Perozo, E. Stefani, ibid., p. 1011; D. Sigg, E. Stefani, F. Bezanilla, *Science* 264, 578 (1994); W. N. Zagotta, T. Hoshi, R. W. Aldrich, *J. Gen. Physiol.* 103, 321 (1994).
18. K. McCormack K., W. J. Joiner, S. H. Heinemann, *Neuron* 12, 301 (1994).
19. W. N. Zagotta, T. Hoshi, J. Dittman, R. W. Aldrich, *J. Gen. Physiol.* 103, 279 (1994).
20. S. K. Aggarwal and R. MacKinnon, *Biophys. J.* 68, A138(1995).

21. S. L. Slatin, X.-Q. Qiu, K. S. Jakes, A. Finkelstein, *Nature* 371, 158 (1994).
22. Unwin, ibid. 373, 37 (1995).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cell comprising an artificial molecular optical sensor, said sensor comprising a predetermined transmembrane cell surface protein comprising a post-translationally generated luminescer at a predetermined residue of said protein, wherein said protein adopts one of a plurality of different interconvertable signal-dependent conformations, whereunder said luminescer provides corresponding different luminescence, wherein said cell comprises a transgene encoding said protein and said cell expresses said protein said residue is located within about 10 residues of a transmembrane domain—extracellular domain junction of said protein.

2. A cell according to claim 1 wherein said protein is a membrane channel protein, a receptor or a signal transducing protein.

3. A cell according to claim 1 wherein said signal is the binding of a ligand to said protein or a change in a charge distribution across the plasma membrane of said cell at said protein.

4. A cell according to claim 1 wherein said residue is not native to said protein.

5. A cell according to claim 1 wherein said residue comprises a functionally available sulfhydryl group.

6. A cell according to claim 1 wherein said residue comprises a functionally available sulfhydryl group and other otherwise functionally available sulfhydryl groups of said cell surface are chemically blocked.

7. A cell according to claim 1 wherein said cell comprises a blocking reagent at residues which would otherwise comprise said luminescer.

8. A cell according to claim 1 wherein said protein is a membrane ion channel protein.

* * * * *